US012285193B2

(12) United States Patent
Biedermann et al.

(10) Patent No.: US 12,285,193 B2
(45) Date of Patent: *Apr. 29, 2025

(54) COUPLING DEVICE FOR COUPLING A ROD TO A BONE ANCHOR

(71) Applicant: BIEDERMANN TECHNOLOGIES GMBH & CO. KG, Donaueschingen (DE)

(72) Inventors: Lutz Biedermann, VS-Villingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 481 days.

This patent is subject to a terminal disclaimer.

(21) Appl. No.: 17/569,832

(22) Filed: Jan. 6, 2022

(65) Prior Publication Data

US 2022/0202452 A1 Jun. 30, 2022

Related U.S. Application Data

(63) Continuation of application No. 17/111,100, filed on Dec. 3, 2020, now Pat. No. 11,246,626.

(Continued)

(30) Foreign Application Priority Data

Dec. 6, 2019 (EP) .................................... 19214198

(51) Int. Cl.
*A61B 17/70* (2006.01)
(52) U.S. Cl.
CPC ...... *A61B 17/7034* (2013.01); *A61B 17/7091* (2013.01); *A61B 17/704* (2013.01)

(58) Field of Classification Search
CPC ............ A61B 17/7001; A61B 17/7032; A61B 17/7034; A61B 17/7035; A61B 17/7037; A61B 17/7074
See application file for complete search history.

(56) References Cited

U.S. PATENT DOCUMENTS

| 5,672,176 A | 9/1997 | Biedermann et al. |
| 8,926,671 B2 | 1/2015 | Biedermann et al. |

(Continued)

OTHER PUBLICATIONS

Extended European Search Report for Application No. 19214198.4, mailed Jun. 16, 2020, 9 pages.

*Primary Examiner* — Ellen C Hammond
(74) *Attorney, Agent, or Firm* — Womble Bond Dickinson (US) LLP

(57) ABSTRACT

A coupling device for coupling a rod to a bone anchor includes a receiving part having a central axis, a coaxial passage, and an engagement recess extending laterally into the passage, and a pressure member having an expandable portion to clamp the head, a radially outwardly facing surface, and an engagement surface extending from the radially outwardly facing surface. The engagement surface of the pressure member is recessed from an outer surface of the receiving part. The pressure member is movable axially from a first position towards a second position where the receiving part directly engages the pressure member to increase a compression force on the expandable portion for clamping an inserted head. The engagement surface of the pressure member is engageable through the engagement recess of the receiving part by the instrument to move the pressure member axially from the second position back towards the first position.

17 Claims, 10 Drawing Sheets

Related U.S. Application Data

(60) Provisional application No. 62/944,592, filed on Dec. 6, 2019.

(56) References Cited

U.S. PATENT DOCUMENTS

| | | | |
|---|---|---|---|
| 8,986,349 B1 | 3/2015 | German et al. | |
| 9,192,413 B2 | 11/2015 | Biedermann et al. | |
| 9,345,516 B2* | 5/2016 | Biedermann | A61B 17/8605 |
| 12,029,452 B2* | 7/2024 | Biedermann | A61B 17/7037 |
| 2008/0269809 A1* | 10/2008 | Garamszegi | A61B 17/8605 |
| | | | 606/301 |
| 2009/0062867 A1* | 3/2009 | Schumacher | A61B 17/7032 |
| | | | 606/301 |
| 2010/0234902 A1* | 9/2010 | Biedermann | A61B 17/7037 |
| | | | 606/305 |
| 2012/0143265 A1* | 6/2012 | Biedermann | B23P 11/005 |
| | | | 606/328 |
| 2017/0172630 A1 | 6/2017 | Biedermann et al. | |
| 2017/0245894 A1* | 8/2017 | Ramsay | A61B 17/7038 |
| 2019/0209214 A1 | 7/2019 | Biedermann et al. | |
| 2019/0247093 A1 | 8/2019 | Jackson et al. | |

* cited by examiner

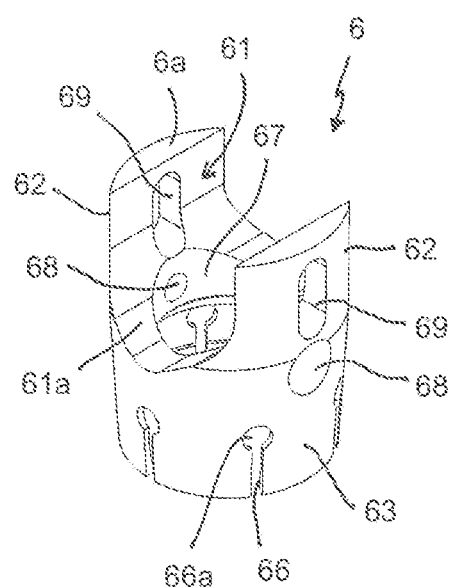
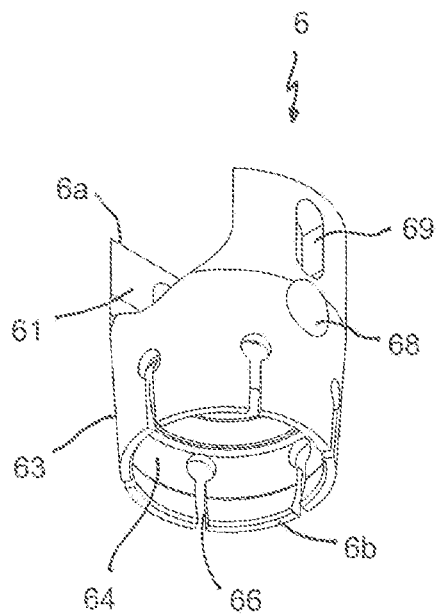
Fig. 9
Fig. 10
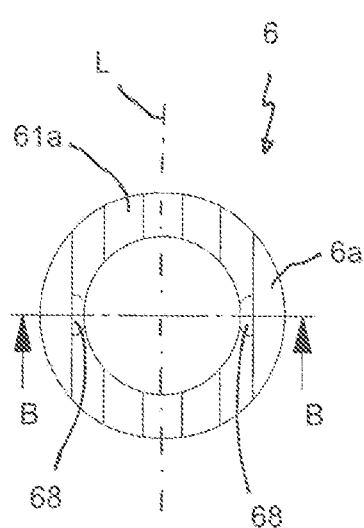
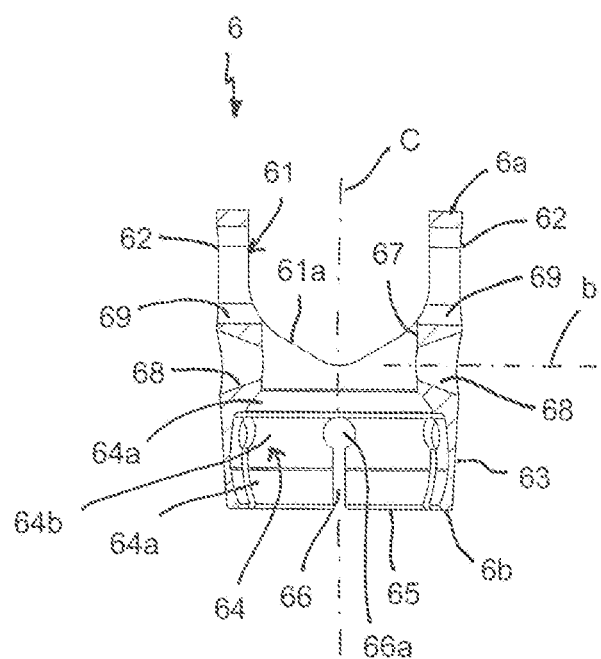
Fig. 11
Fig. 12

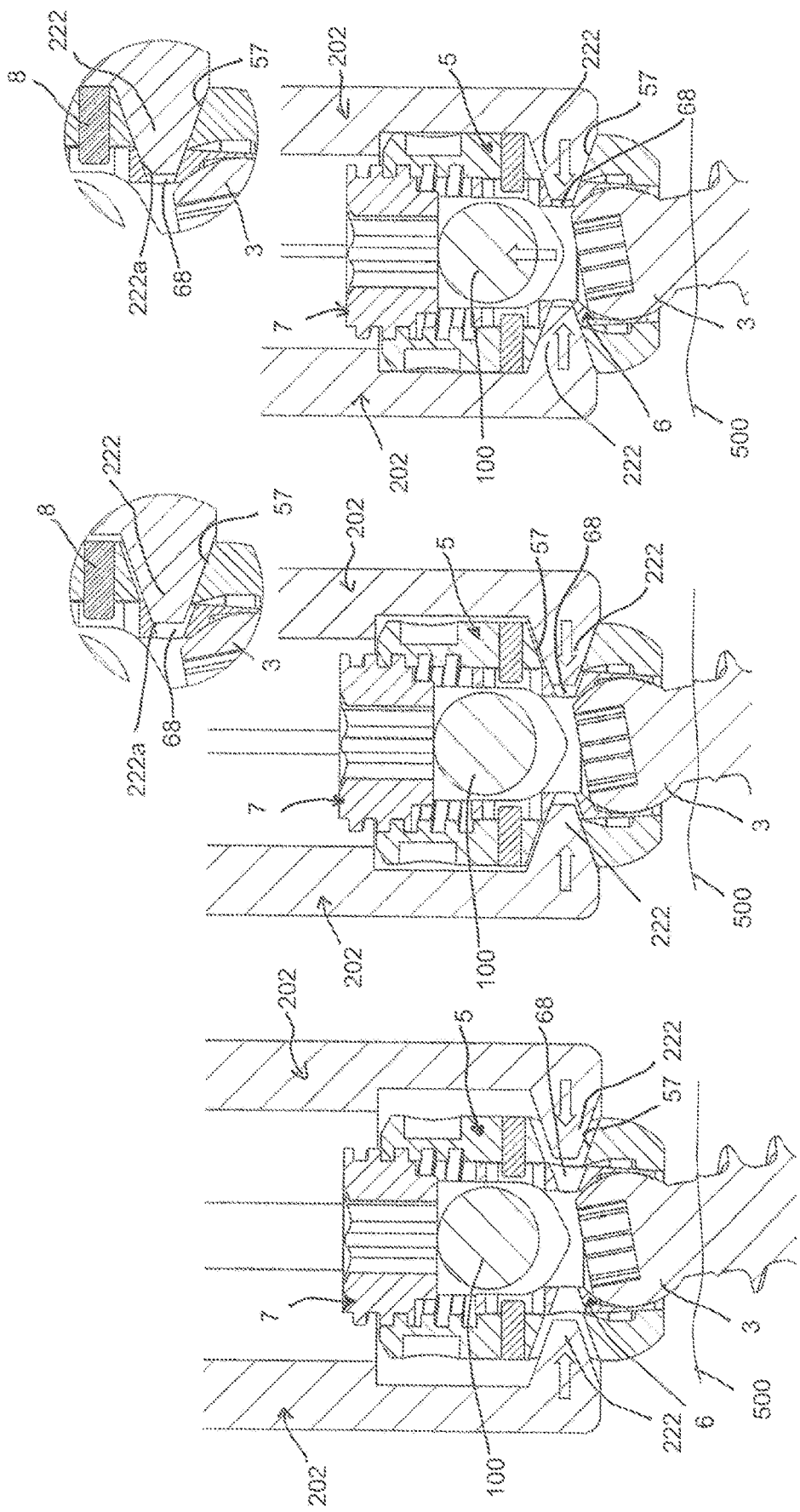

COUPLING DEVICE FOR COUPLING A ROD TO A BONE ANCHOR

CROSS-REFERENCE TO RELATED APPLICATION(S)

This application is a continuation of U.S. patent application Ser. No. 17/111,100, filed Dec. 3, 2020, which claims priority to and the benefit of U.S. Provisional Patent Application No. 62/944,592, filed Dec. 6, 2019, the contents of which are hereby incorporated by reference in their entirety, and claims priority from European Patent Application EP 19 214 198.4, filed Dec. 6, 2019, the contents of which are hereby incorporated by reference in their entirety.

BACKGROUND

Field

The application relates to a coupling device for coupling a rod to a bone anchor, and more particularly relates to a polyaxial bone anchoring device, wherein a head of the bone anchor can be provisionally locked with respect to the coupling device and can be unlocked from such a provisional locking configuration. The invention also relates to a system including the coupling device or the polyaxial bone anchoring device and an instrument.

Description of Related Art

U.S. Pat. No. 5,672,176 describes an anchoring member for connecting a rod with a bone screw, that includes a screw member and a seat part receiving a screw head of the screw member and a rod. The anchoring member further includes a pressure member formed to embrace the screw head. The seat part has a tapering portion and the pressure member has an outer conical surface in a region laterally surrounding the screw head. The conical surface tapers with a cone angle corresponding to the cone angle of the surface of the seat part. When the conical surfaces engage each other, a movement of the screw head is blocked even if a swivel nut is loosened for readjusting the rod.

A polyaxial bone anchoring device with a function of pre-locking a head of a bone anchor is known, for example, from U.S. Pat. No. 8,926,671 B2. The polyaxial bone anchoring device includes a receiving part including a receiving part body with a channel for receiving a rod and an accommodation space for accommodating the head of the bone anchor, and a pressure element arranged at least partially in the accommodation space. The pressure element has a flexible portion to clamp the head and can assume a pre-locking position to clamp the head in the receiving part by a pre-stress exerted by the pressure element onto the head. In the pre-locking position, an outer surface portion of the pressure element and an inner surface portion of the receiving part body are engaged. In one example, the surfaces can be tapered. Locking of the head is achieved via a locking member.

U.S. Pat. No. 9,345,516 B2 describes a polyaxial bone anchoring device, wherein a temporary clamping of a head of an anchoring element in a desired angular position with respect to a receiving part without locking the head can be achieved. The polyaxial bone anchoring device includes a set screw that is threadable into a through hole of the receiving part and that engages a hole in the pressure element such that a force is exerted by the pressure element onto the head that maintains the head at an adjustable angular position.

SUMMARY

While the known polyaxial bone anchoring devices exhibit some aspects of locking or provisionally locking the head of the bone anchor while allowing correction steps to be carried out, there is still a need for a polyaxial bone anchoring device that provides more options for carrying out correction steps during surgery more easily and/or repeatedly.

It is therefore an object of the invention to provide an improved coupling device for a polyaxial bone anchoring device, the polyaxial bone anchoring device, and a system including such a coupling device or polyaxial bone anchoring device and an instrument.

According to an embodiment, a coupling device for coupling a rod to a bone anchor includes a receiving part having a channel for receiving a rod, a passage defining a central axis, and an accommodation space for a head of the bone anchor. The receiving part includes an outer surface with an engagement structure configured to be engaged by an instrument. The coupling device further includes a pressure member configured to be arranged at least partially in the accommodation space. The pressure member has a flexible portion defining a hollow interior to accommodate and clamp the head therein and an outer surface with an engagement structure configured to be engaged by the instrument. In the receiving part, the pressure member can assume a first position in which an inserted head is clamped or locked with a first locking force or is freely pivotable, and a second position in which the pressure member engages an inner wall portion of the passage such that the flexible portion is compressed to clamp or lock an inserted head with a locking force that is greater than the first locking force, and wherein the pressure member is movable from the second position back towards the first position by engagement with the instrument.

The coupling device permits easy unlocking of an inserted head. Also, a clamping and/or locking step and an unlocking step can be carried out repeatedly. The clamping or locking step can be carried out easily, for example, using a rod inserted into the channel and/or a locking member. For the unlocking step, the instrument may be used. The instrument works reliably in any situation or level of locking, such as full locking of the head or only frictional clamping of the head.

The instrument is configured to laterally engage the pressure member. Therefore, the unlocking step can be effected when the rod is not in the channel or when the rod is at an elevated position relative to a bottom of the channel.

With the instrument and the coupling device, the unlocking step can be precisely carried out, as the forces that are necessary for unlocking are automatically generated due to the geometry and position of the pressure member relative to the receiving part.

In a specific embodiment, engagement structures for the instrument that are provided at the pressure member and the receiving part, respectively, may be offset from each other in an axial direction. This leads to an automatic centering and/or aligning of the respective engagement structures when the instrument successively engages the engagement structure of the receiving part and the engagement structure of the pressure member.

The polyaxial bone anchoring device is preferably of the bottom-loading type, which means that the head of the bone anchor is inserted from a bottom opening of the receiving part into the accommodation space. Hence, a modular system can be provided where any type of bone anchor that has a head can be combined with the coupling device to provide a polyaxial bone anchoring device.

A particular application of the coupling device, the polyaxial bone anchoring device, and the system including the coupling device or the polyaxial bone anchoring device and the instrument may be in the field of spinal surgery.

BRIEF DESCRIPTION OF THE DRAWINGS

Further features and advantages of the invention will become apparent from the description of embodiments by means of the accompanying drawings. In the drawings:

FIG. 9 shows a perspective view from a top of a pressure member of the polyaxial bone anchoring device of FIGS. 1 to 4.

FIG. 10 shows a perspective view from a bottom of the pressure member of FIG. 9.

FIG. 11 shows a top view of the pressure member of FIGS. 9 and 10.

FIG. 12 shows a cross-sectional view of the pressure member of FIGS. 9 to 11, the cross-section taken along line B-B in FIG. 11.

FIGS. 19a to 19c show steps of unlocking a head of the bone anchor relative to the coupling device using the instrument of FIGS. 3 and 13 to 16.

DETAILED DESCRIPTION

Figures 1, 2:
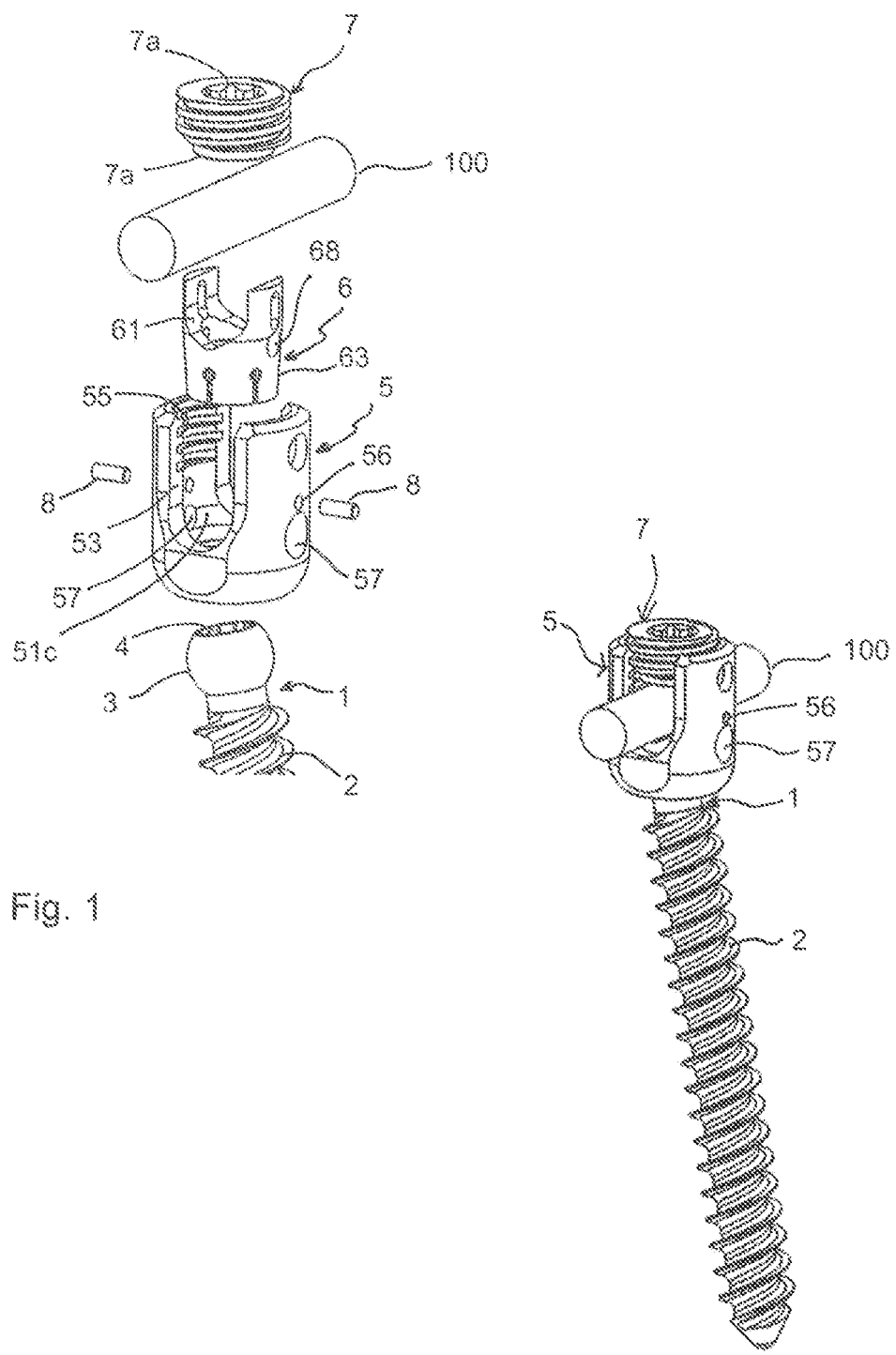
FIG. 1 shows an exploded perspective view of a polyaxial bone anchoring device according to an embodiment.
FIG. 2 shows the polyaxial bone anchoring device of FIG. 1 in an assembled state.
Figure 3:
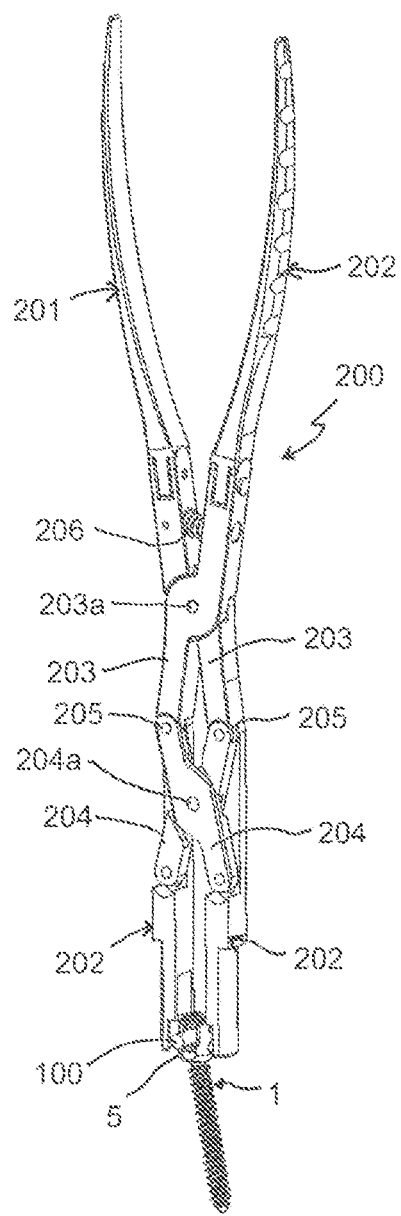
FIG. 3 shows a perspective view of a system including the polyaxial bone anchoring device of FIGS. 1 and 2 and an instrument.

A polyaxial bone anchoring device according an embodiment is generally shown in FIGS. 1 to 3, and includes a bone anchoring element 1 in the form of a screw member having a shank 2 which is at least partially threaded and a head 3. The head 3 has a spherical outer surface portion. In greater detail, in the embodiment, the head 3 is shaped as a spherical segment with a substantially flat end surface in which a recess 4 for engagement with a tool may be provided. The bone anchoring device further includes a coupling device for connecting the bone anchoring element 1 to a rod 100. The coupling device includes a receiving part 5 and a pressure member 6 that is configured to be arranged in the receiving part 5 and is further configured to exert pressure onto the head 3. In addition, for securing the rod 100 in the receiving part 5 and for exerting pressure onto the rod 100 and the pressure member 6, a locking member 7 in the form of, for example, a set screw which cooperates with the receiving part 5 may be provided. The locking member 7 may have a tool engagement recess 7a. The pressure member 6 may be secured and/or aligned in the receiving part by means of a securing element, for example, by pins 8.

As shown in FIG. 3, an embodiment of a system includes the polyaxial bone anchoring device as shown in FIGS. 1 and 2 and an instrument 200. The instrument 200 is configured to engage the receiving part 5 and the pressure member 6 to move the pressure member 6 relative to the receiving part 5.

As illustrated in particular in FIGS. 5 to 8, the receiving part 5 is substantially cylindrical and has a first end or top end 5a, a second end or bottom end 5b, and a passage 51 extending from the top end 5a towards the bottom end 5b, the passage defining a longitudinal central axis C. The passage 51 extends completely from the top end 5a to the bottom end 5b, thereby forming an opening 52 at the bottom end 5b. Adjacent to the top end 5a, a substantially U-shaped recess 53 is provided that extends towards the second end 5b to a bottom 53a. The passage 51 may have sections with different diameters. In the embodiment shown, a first section 51a may have a substantially constant diameter and extends from the top end 5a to an axial height above or corresponding approximately to the height of the bottom 53a of the U-shaped recess 53. Below the first section 51a, a second section 51c may be provided that narrows towards the bottom end 5b. In greater detail, in the embodiment, the second section 51c tapers, preferably conically, towards the bottom end 5b. Within the second section 51c, a widened section 51b is formed that widens towards the bottom end 5b. Hence, the narrowing regions of the second section 51c are divided into a portion above the widened section 51b and a portion below the widened section 51b. The widened section 51b provides an accommodation space for a portion of the pressure member 6 which can expand therein. The difference in diameter between the widened section 51b and the second section 51c forms an edge 51d that protrudes into the passage 51. The substantially U-shaped recess 53 divides the upper portion of the receiving part 5 into two free legs 54 and forms a channel for receiving the rod. An internal thread 55, for example, a square thread, may be formed on an inner wall portion of the legs 54, preferably adjacent to the top end 5a, for cooperating with the locking member 7. An axial length of the tapered second section 51c may be such that, in cooperation with the pressure member 6, a locking force may be generated that is configured to compress a portion of the pressure member for frictionally clamping and/or firmly locking the head 3 in the pressure member 6.

At a distance above the bottom 53a of the U-shaped recess, two opposite transverse holes 56 extend completely through the wall of the receiving part 5. The transverse holes 56 are configured to receive the pins 8.

The receiving part 5 further includes at least one, two in the embodiment shown, engagement structures 57 for engagement with the instrument 200. The engagement structures 57 are formed as narrowing holes or bores extending completely from an outer surface of the receiving part through a wall of the receiving part into the passage 51. The engagement structures 57 may narrow in a conical shape which tapers and narrows from outside the receiving part towards the passage. Preferably, the shape of each engagement structure is substantially that of a hollow truncated cone. Two such holes may be provided 180° offset from each other in a circumferential direction around the central axis C. In this embodiment, the engagement structures 57 extend in a direction perpendicular to a plane including a channel axis L of the U-shaped recess 53 and the central longitudinal axis C. More specifically each engagement structure 57 has a central transverse hole axis a that extends perpendicular to the central axis C. Moreover, the engagement structures 57, or more specifically the hole axes a, are at an axial position Ha with respect to the bottom end 5b. The holes may be symmetrical around the hole axis a. The axial height Ha may be such that the hole axis a is above the bottom 53a of the U-shaped recess 53, and preferably the hole axis a may be at least partially within the second section 51c, or in other words, in a narrowing section of the passage 51. An inner size of the engagement structure 57 is such that a front portion of the instrument 200 can be received therein in a substantially form-fit manner, as discussed in greater detail below. Hence an inner wall of the engagement structures 57 form guiding surfaces, respectively, for a portion of the instrument.

Finally, at the same circumferential position as the engagement structures 57 and in an axial position closer to the top end 5a, tool engagement recesses 58 may be formed in the outer surface of the receiving part 5. The tool engagement recesses 58 may have, for example, a circular contour.

Referring now to FIGS. 9 to 12 the pressure member 6 will be described in greater detail. In the embodiment, the pressure member 6 is a monolithic part. The pressure member 6 has a first end or upper end 6a and an opposite or lower end 6b. Adjacent to the upper end 6a, the pressure member 6 has a substantially cylindrical outer shape with an outer diameter only slightly smaller than an inner diameter of the first section 51a of the passage 51, such that the cylindrical portion of a pressure member fits into the first section 51a and can move or slide therein. Adjacent to the upper end 6a, a substantially V-shaped recess 61 for the rod 100 is provided. More specifically, a base 61a of the recess 61 has a substantially V-shaped contour. Thereby rods 100 of different diameter can selectively be supported on the base 61a. Such rods (not shown) rest on the base 61a along substantially two longitudinal contact lines. A rod that is supported in this manner may be prevented from moving sideways. Sidewalls of the recess 61 may be substantially vertical, and the deepest portion of the base 61a may be rounded. By means of the V-shaped recess 61, upstanding legs 62 are formed which may have a height, or in other words, the substantially V-shaped recess 61 may have a depth, such that the top end 6a of the pressure member is below a highest point of an outer surface of an inserted rod 100 when the rod rests on the base 61a.

The lower portion of the pressure member 6 has a narrowing outer surface 63 that narrows towards the bottom end 6b. More specifically, the surface 63 is a conical outer surface that tapers towards the bottom end 6b. The outer surface 63 is configured to cooperate with the narrowing second section 51c of the passage 51 of the receiving part 5. Adjacent to the bottom end 6b, there is a hollow interior section 64 for accommodating the head. The hollow interior section 64 may have substantially spherically-shaped sections 64a that match the spherical shape of the outer surface portion of the head 3 and a slightly enlarged section 64b to facilitate pivoting of the head. The hollow interior section 64 has an opening 65 at the bottom end 6b. A plurality of slits 66 which are open towards the bottom end 6b extend in an axial direction along the wall of the pressure member 6 in the region of the hollow interior section 64. A length of the slits 66 in the longitudinal direction may be such that, when the head 3 is inserted, the slits extend above a region of the head 3 with a greatest outer width. Further, the slits 66 may each have a widened end portion 66a to render the lower portion of the pressure member 6 more flexible, in a manner such that the lower portion can be expanded and compressed. Hence, the lower portion of the pressure member forms a flexible portion. The size of the hollow interior 64 may be such that when the head 3 is inserted through the opening 65, the flexible portion snaps onto the head and slightly clamps the head 3 by friction.

For providing access to the tool engagement recess 4 of the head 3, the pressure member 6 defines a coaxial bore 67. The coaxial bore 67 may extend from the substantially V-shaped recess 61 into the hollow interior section 64.

In addition, the pressure member 6 includes at least one engagement structure, with two opposite engagement structures 68 in the embodiment shown. The engagement structures 68 are configured to be engaged by a front portion of the instrument 200. In greater detail, the engagement structures 68 in the embodiment are formed as conical holes or bores that extend through the wall of the pressure member 6 from the outside to the coaxial bore 67. A transverse central axis b of the holes may be located at an axial position slightly below the deepest portion of the base 61a of the substantially V-shaped recess 61. More specifically, the axial position of the engagement structures 68 is at least partially within the narrowing outer surface 63. The transverse central axes b of the engagement structures 68, respectively, extend substantially perpendicularly to the longitudinal L defined by the recess 61.

A diameter of the holes at the outer surface of the pressure member 6 substantially corresponds to a diameter of the holes at the receiving part 5 at a location of the passage. Hence, when the pressure member 6 is in the receiving part 5 at an axial position where the axes a of the holes in the receiving part 5 and the axes b of the holes in the pressure member 6 are at a same height, the holes of the receiving part 5 generally align with and are substantially flush with the holes of the pressure member 6, forming a continuous hollow space, preferably a hollow cone.

Moreover, the pressure member defines two elongate recesses 69 in the center of each of the legs 62 which are opposite to each other and are aligned such that a longer side of the elongate recesses 69 is substantially parallel to the central axis C of the receiving part 5. The ends of the elongate recesses 69 may be rounded. A width and length of the elongate recesses 69 is such that the pins 8 can be received therein and moved in the axial direction.

Figure 4:
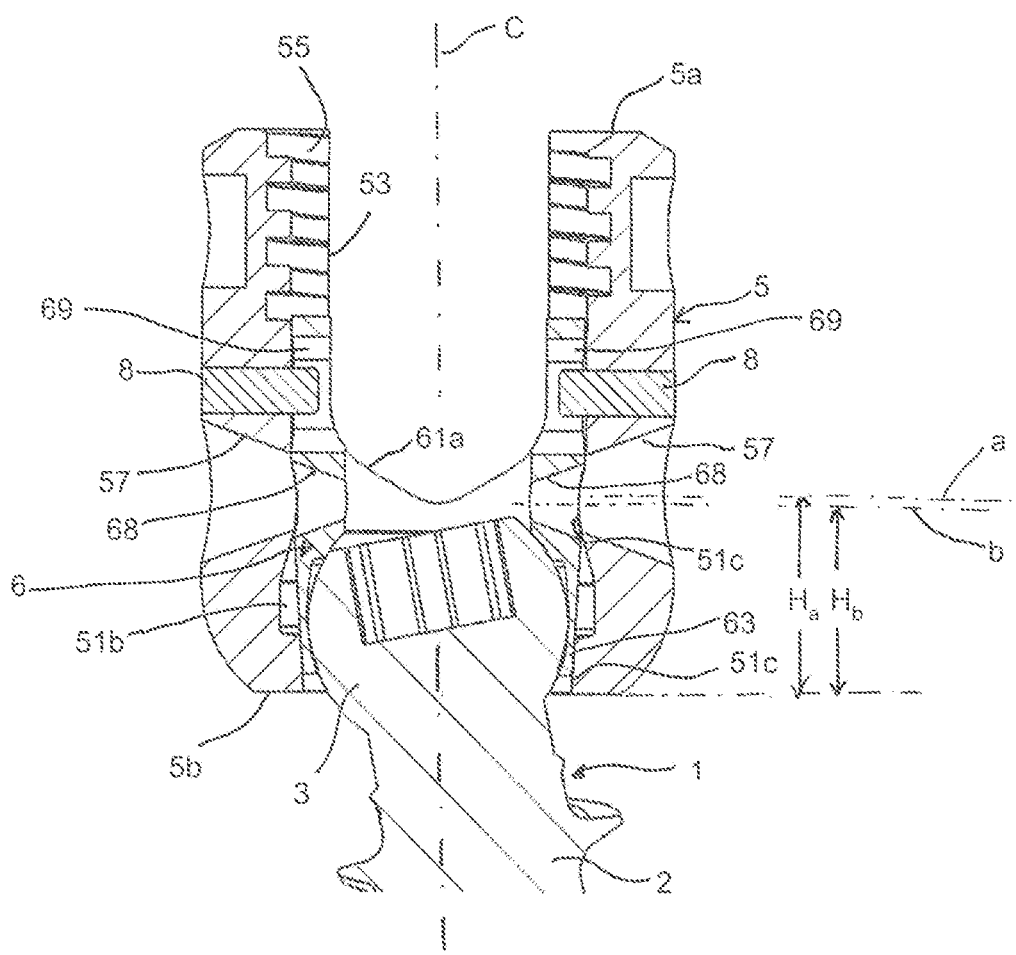
FIG. 4 shows a cross-sectional view of the polyaxial bone anchoring device of FIGS. 1 to 3, the cross-section taken in a plane including a central longitudinal axis of a receiving part of the polyaxial bone anchoring device and perpendicular to a longitudinal axis of a rod channel of the receiving part.
Figure 5:
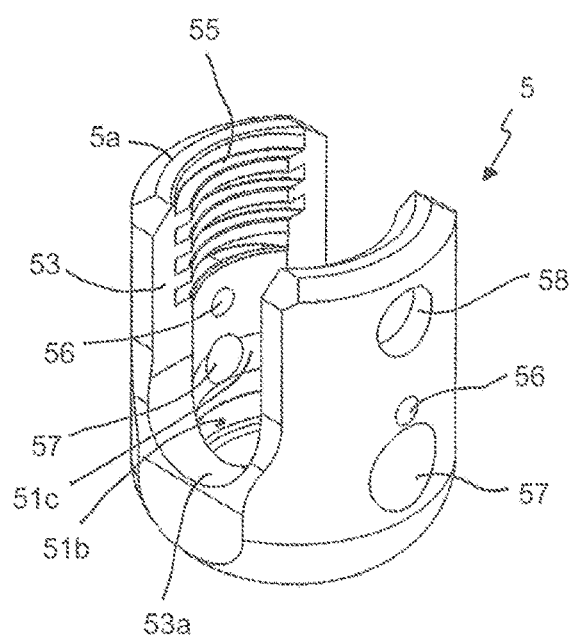
FIG. 5 shows a perspective view from a top of the receiving part of the polyaxial bone anchoring device of FIGS. 1 to 4.
Figure 6:
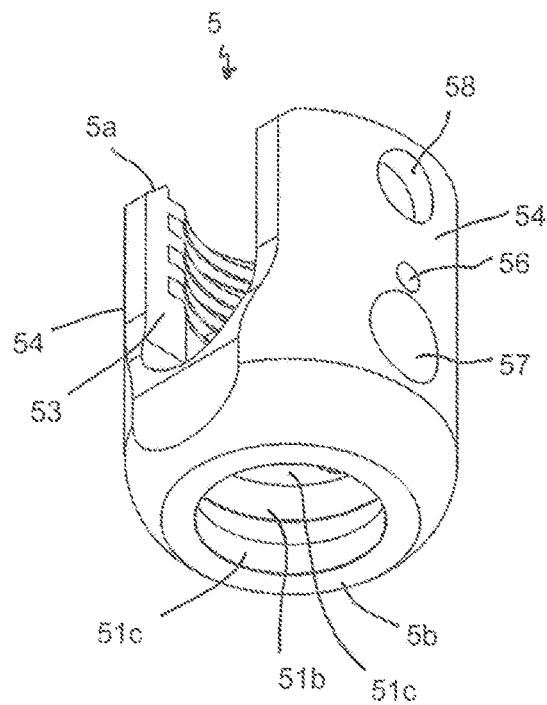
FIG. 6 shows a perspective view from a bottom of the receiving part of FIG. 5.
Figure 7:
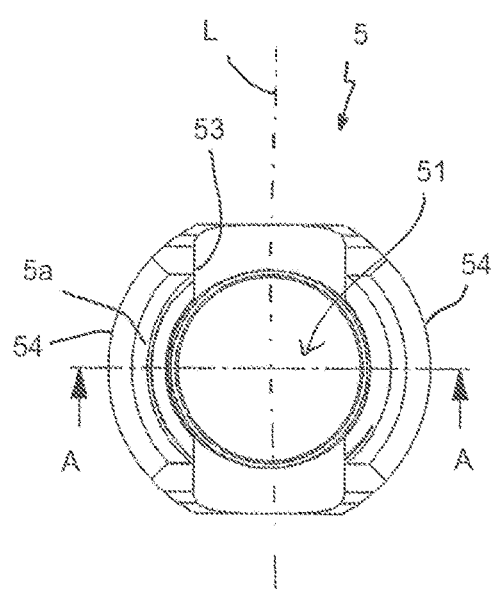
FIG. 7 shows a top view of the receiving part of FIGS. 5 and 6.
Figure 8:
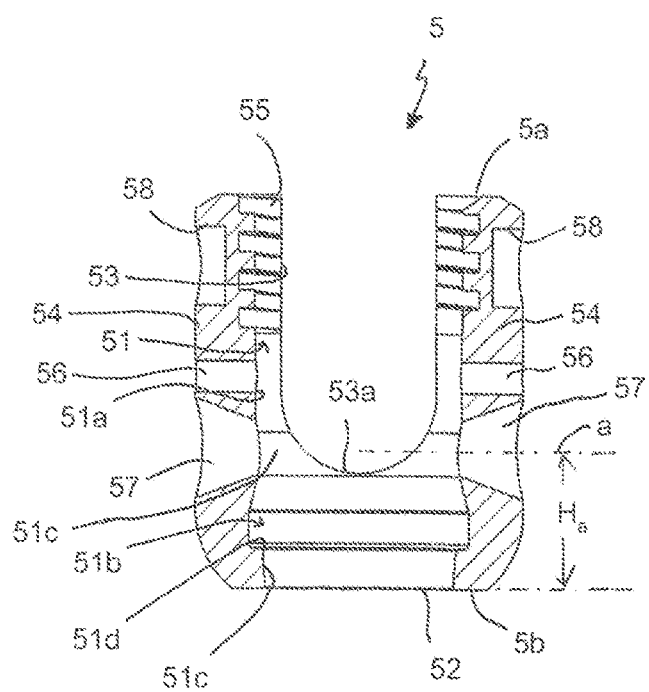
FIG. 8 shows a cross-sectional view of the receiving part of FIGS. 5 to 7, the cross-section taken along line A-A in FIG. 7.
Figure 13:
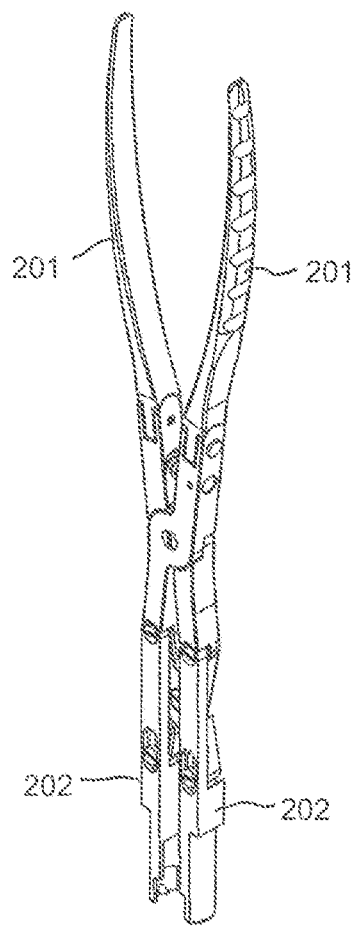
FIG. 13 shows a perspective view of the instrument of FIG. 3, seen from a side opposite to the side shown in FIG. 3.

Turning back to FIG. 4, the dimensions of the pressure member 6 and the dimensions of the receiving part 5 are selected such that when the pressure member 6 is in the receiving part 5, the head 3 is inserted into the hollow interior section 64 of the pressure member and the narrowing surfaces of the second section 51c of the receiving part and the narrowing outer surface 63 of the pressure member 6 are engaged to some extent, the head 3 is clamped or firmly locked depending on the extent of the engagement. It shall be noted that the narrowing, preferably conical, shape of the pressure member that extends along at least the axial length of the flexible portion and that cooperates with the narrowing, preferably conical, second section 51c in the receiving part over an axial length greater than a length of the flexible sections results in a reliable or strong clamping of the head. As shown in FIG. 4, the engagement structures 68 of the pressure member 6 and the engagement structures 57 of the receiving part 5 are offset from each other in the axial direction. In greater detail, the engagement structure 57 of the receiving part is at a slightly higher axial position Ha compared to the position $H_b$ of the engagement structure 68 of the pressure member 6. This defines a position of the pressure member relative to the receiving part in which the head 3 is clamped and can be pivoted only by overcoming a friction force, or may even be fully locked.

Referring now to FIGS. 13 to 16, the instrument 200 may be implemented as a hand-held instrument in the form of tongs having a pair of handles 201 at one end and a pair of claws 202 forming a front portion at an opposite end. Between the handles 201 and the claws 202, two pairs of levers are arranged (see also FIG. 3). A first pair of levers 203 is configured to pivot around a pivot axis 203a and are connected at one side to the handles 201, respectively, and at an opposite side to a second pair of levers 204. The second pair of levers 204 is configured to pivot around a pivot axis 204a. The second pair of levers 204 is connected to the first pair of levers 203 through pivots or hinges 205 and is connected at an opposite end to the claws 202. By means of this, the claw on one side is connected to the handle on the same side and the claw on the other side is connected to the handle on the other side. With this construction, moving of the handles 201 towards one another causes the claws 202 to move towards each other as well, thereby being aligned to be substantially parallel. The instrument may include a spring 206 that holds the claws 202 in an open position, the spring force of which must be overcome by the handles 201 to close the claws 202.

Figure 14:
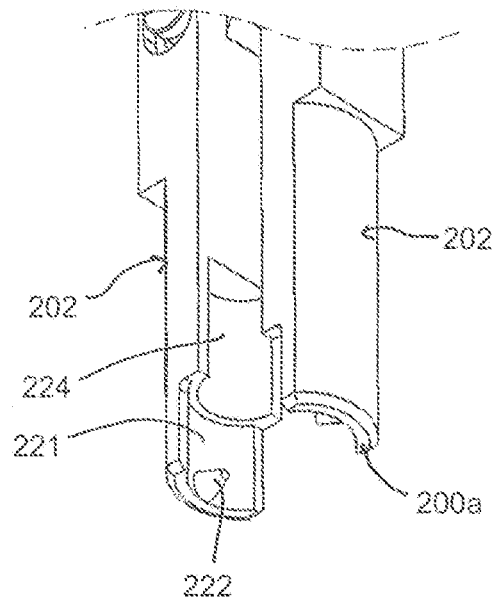
FIG. 14 shows a perspective view from a bottom of a front portion of the instrument of FIGS. 3 and 13.
Figure 15:
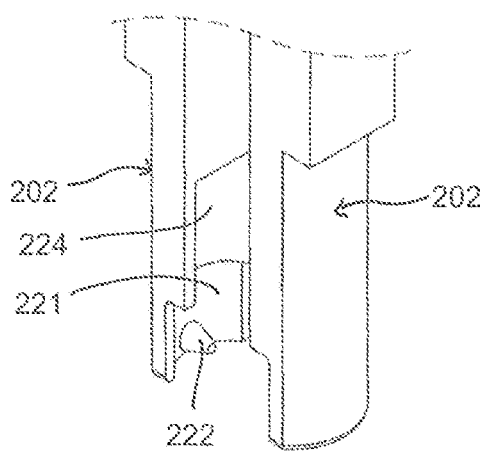
FIG. 15 shows a perspective view from a top of the front portion of the instrument of FIGS. 3, 13, and 14.
Figure 16:
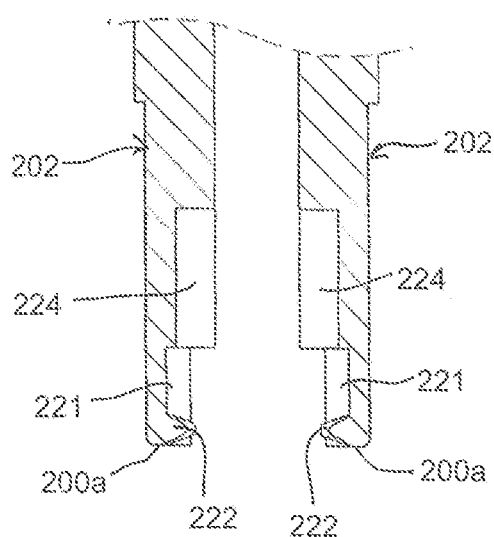
FIG. 16 shows a cross-sectional view of the front portion of the instrument of FIGS. 3 and 13 to 15, where the cross-section is taken in a plane containing a central longitudinal axis of the instrument and extending through centers of two end portions of the instrument.

As shown in greater detail in FIGS. 14 to 16, a front portion of the instrument 200 includes the claws 202. The claws 202 are configured to engage the receiving part 5 from an outside thereof. To accomplish this, the claws 202 each defines a cylindrical recess 221 adjacent to a front end 200a which is adapted or shaped to correspond to the outer shape of the receiving part 5. Adjacent to the front end 200a, at an inner wall of the cylindrical recesses 221, an engagement structure 222 is provided. The engagement structure 222 is configured to engage engagement structure 57 at the receiving part and the engagement structure 68 at the pressure member 6. Specifically, the engagement structure 222 may be a conical peg that is adapted or shaped to correspond to the hollow conical shape of the conical holes of the receiving part and the pressure member. To accomplish this, the engagement structure 222 is located at approximately the center of each claw 202 in the circumferential direction. Adjacent to the cylindrical recess 221 on a side opposite the front end 200a, the claws 202 may define a further cylindrical recess 224. The cylindrical recess 224 may have a smaller diameter than the cylindrical recess 221. During engagement of the claws with the receiving part, the second cylindrical recess 224 may provide space for accommodating a portion of the locking member 7 therein.

The locking member 7 may have a projection 7b at a bottom side thereof (see FIG. 1) that serves for elongating the locking member 7, to permit the fixation of rods of smaller and greater diameters in the rod receiving recess 53 using the same locking member. Hence, when a rod of greater diameter is received, the locking member 7 may protrude out of the first end 5a of the receiving part 5.

The parts and portions of the bone anchoring device and the instrument may be made of any material, preferably, however, of a bio-compatible material, such as for example, titanium or stainless steel, or any other bio-compatible metal or metal alloy, for example, or a plastic material. For a bio-compatible alloy, a NiTi alloy, for example Nitinol, may be used. Other materials that can be used may be magnesium or magnesium alloys. Bio-compatible plastic materials for use may be, for example, polyether ether ketone (PEEK) or poly-L-lactide acid (PLLA). The parts can be made of the same or of different materials from one another.

In use, at least two bone anchoring devices may be anchored in bone and connected through a rod. As the bone anchoring device according to the embodiment described is a bottom-loading bone anchoring device, the head of the bone anchor 1 is inserted from the bottom end 5b into the receiving part. This can be done prior to insertion of the shank into the bone. Alternatively, the shank can already be inserted into a vertebra or other bone, and the coupling device can then be mounted onto the head 3.

Figure 17C:
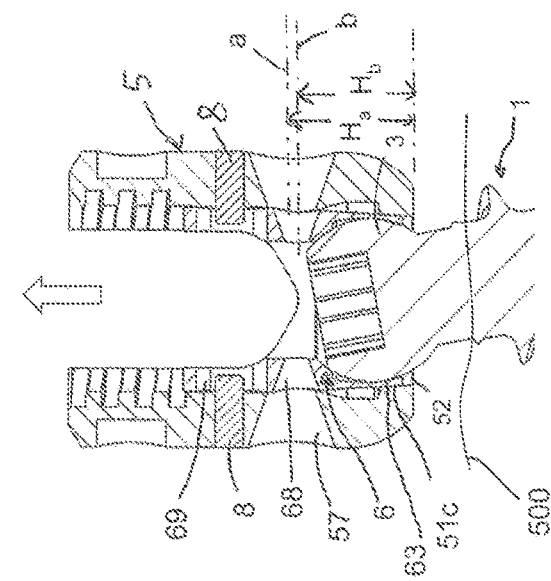
FIGS. 17a to 17c show steps of mounting a coupling device of the polyaxial bone anchoring device of FIGS. 1 to 4 onto a bone anchor that has been inserted into bone.
Figure 17B:
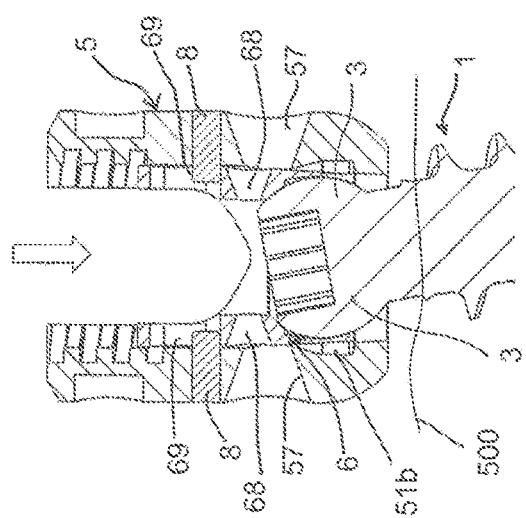
Figure 17A:
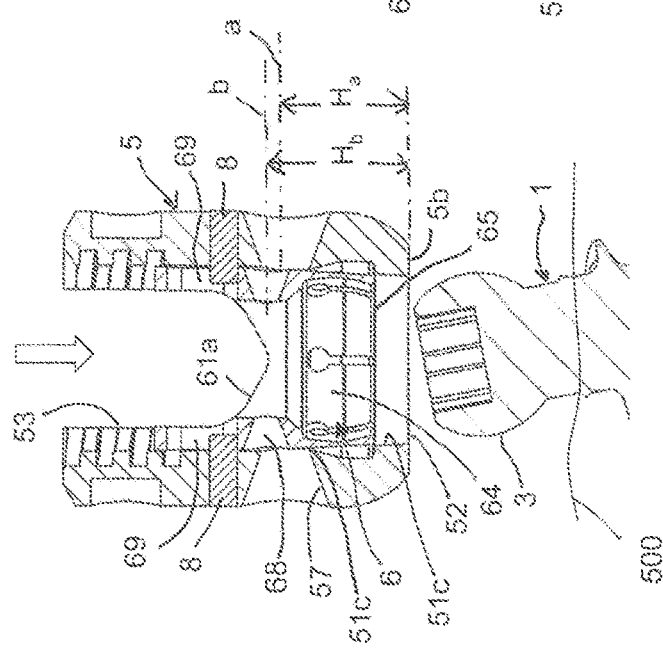

Referring to FIGS. 17a to 17c, steps for mounting the coupling device to the bone anchor are shown. The bone anchor 1 has been inserted into bone 500, where the head 3 protrudes out of the bone surface. The coupling device may be preassembled, where the pressure member has been inserted into the passage to an extent such that the flexible portion is located in the widened section 51b of the passage 51 that forms an accommodation space. The pins 8 are placed in the holes 56, where their front ends extend into the recesses 69 of the pressure member 6. Thus, the recess 53 of the receiving part and the recess 61 of the pressure member are aligned. The rear ends of the pins may be flush with the outer surface of the receiving part. As depicted in FIG. 17a, the pressure member 6 is at a highest position relative to the bottom end 5b of the receiving part 5. This highest position defines an insertion position where the head 3 can be inserted. In the insertion position the lower ends of the recesses 69 of the pressure member 6 abut against the inserted pins 8. The engagement structure 68 of the pressure member is at an axial height $H_b$ that is above an axial height Ha of the engagement structure 57 of the receiving part 5 relative to the bottom end 5b. As depicted in FIG. 17b, the coupling device is placed onto the head 3. The pins 8 serve as abutment for the pressure member 6. When the head 3 enters into the hollow interior 64, the flexible portion can expand in the accommodation space 51b. Finally, as shown in FIG. 17c, the coupling device is pulled upwards relative to the head 3. As the head 3 is clamped in the flexible portion of the pressure member, the receiving part 5 is moved slightly upwards so that the narrowing surface in the second section 51*c* of the passage 51 and the narrowing surface 63 at the outside of the pressure member engage. Thereby, the head 3 is clamped by friction and can pivot only by overcoming the friction force. Simultaneously, the head 3 can no longer escape through the lower opening 52 of the receiving part 5, since the bottom of the pressure member blocks the head 3 from doing so.

Figure 18C:
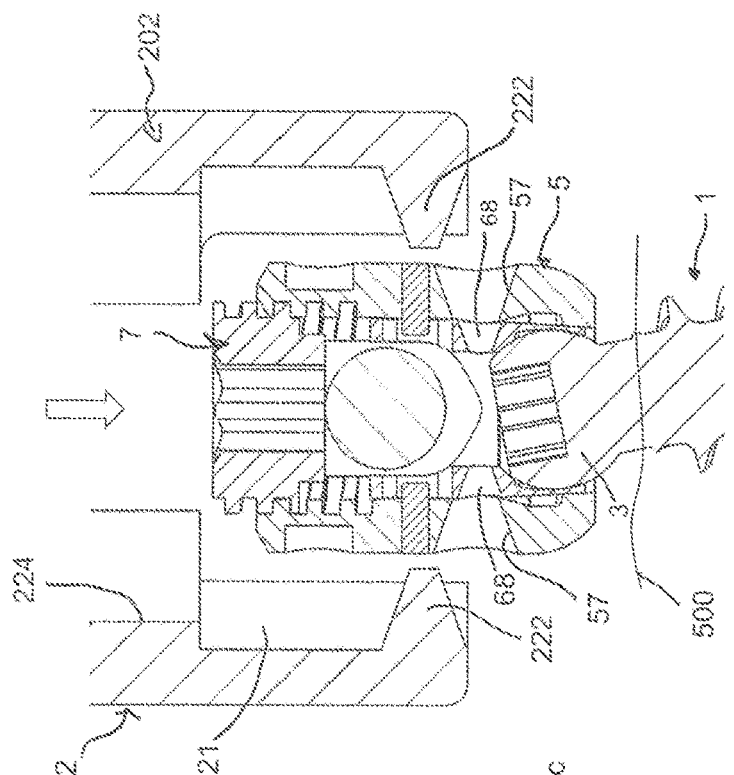
FIGS. 18a to 18c show steps of locking the bone anchor relative to the coupling device with a locking member and then loosening the locking member.
Figure 18B:
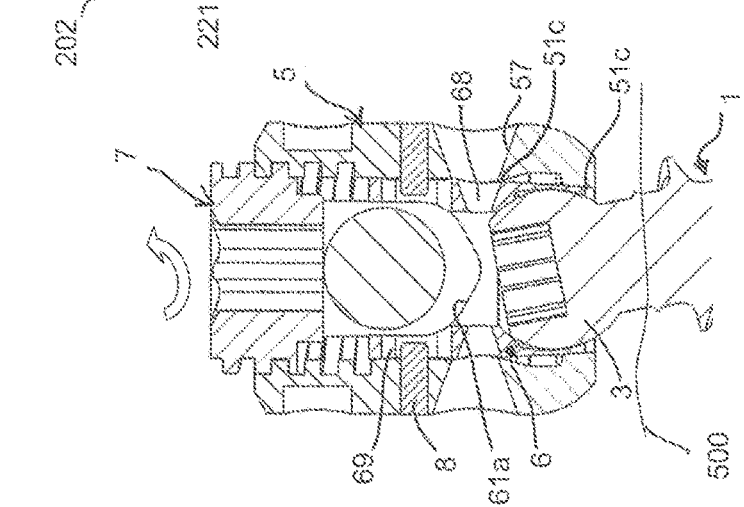
Figure 18A:
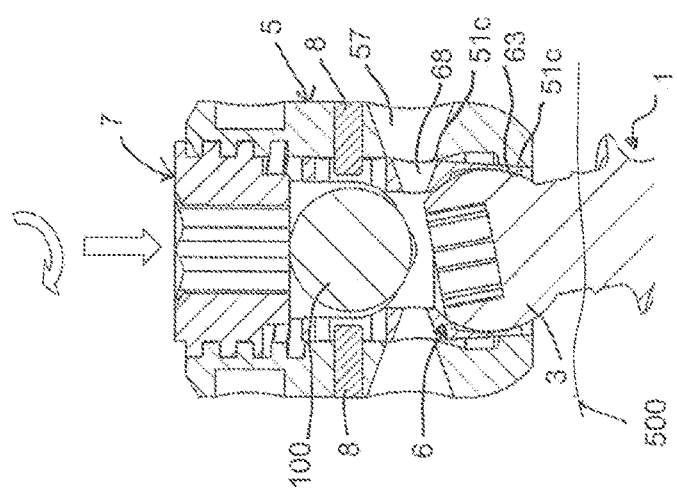

Referring to FIGS. 18*a* and 18*b*, steps of locking the polyaxial bone anchoring device are shown. In FIG. 18*a*, the rod 100 is inserted and the locking member 7 is screwed in between the legs 54 of the receiving part 5. Tightening the locking member 7 results in a pressure exerted through the rod onto the pressure member 6. Thereby, the pressure member 6 is pushed deeper towards the bottom end 5*b*, with the narrowing outer surface 63 of the flexible portion being urged deeper into the narrowing second section 51*c* of the passage. This results in a compression of the flexible portion of the pressure member around the head 3, which locks the head 3 in the receiving part 5 and holds the shank 2 at a specific angular position relative to the central axis C. As shown in FIG. 18*b*, unscrewing or removing the locking member 7 allows the rod 100 to move up in an axial direction and/or to be removed completely from the receiving part. For example, the rod 100 can assume an axial position above the base 61*a* so that it no longer rests on the base 61*a*. Hence, various correction steps can be carried out with the rod not being present at all or being at an elevated position in the channel. When the head 3 is locked or provisionally locked, the engagement structure 68 of the pressure member 6 is moved downward relative to the engagement structure 57 of the receiving part 5. In the embodiment, in the locked or provisionally locked configuration, the axial position of the engagement structure 57 of the receiving part 5 is higher than the axial position of the engagement structure 68 of the pressure member 5. Hence, in the locked or provisionally locked configuration, the engagement structures of receiving part and pressure member are offset from each other in a way such that bringing them into alignment with each other results in unlocking of the head 3, for example, by moving the pressure member axially upwards.

Next, as shown in FIG. 18*c*, the claws 202 are moved in an open state towards the receiving part 5 and oriented such that the pegs 222 are circumferentially aligned with the engagement structure 57 of the receiving part.

FIG. 19*a* shows that the pegs 222 of the claws 202 engage the engagement structure 57 of the receiving part. The rod 100 may be at an elevated position, and the locking member 7 may protrude into the cylindrical recess 224. As shown in FIGS. 19*a* and 19*b*, actuating the handles 201 of the instrument 200 moves the claws from both sides inwardly towards the central axis, while for example, the claws may remain substantially parallel with one another. The pegs 222 extend through the holes of the receiving part 5 and enter into the holes of the pressure member 6. Because of the offset of the axial position of the hole axes (e.g., where the holes of the pressure member 6 are below the holes of the receiving part 5), an upper front edge portion 222*a* of the pegs 222 abuts against an upper wall of the hole of the pressure member 6 as depicted in the enlarged portion of FIG. 19*b*. Thus, the upper wall of the engagement structure 68 of the pressure member 6 forms a guiding surface for guiding the engagement portion 222 of the instrument.

Finally, as shown in FIG. 19*c*, the engagement of the engagement structure 57 at the pressure member with the engagement portion 222 of the instrument leads to alignment of the engagement structures of the receiving part and the pressure member, as depicted in greater detail in the enlarged portion of FIG. 19*c*. Thereby, a force is generated that moves the pressure member 6 upward relative to the receiving part 5 to a position in which the engagement structures are aligned. When the pressure member is moved upwards, the compression of the head 3 is decreased and the head is unlocked. It shall be noted that, depending on the dimensions of the pressure member and the receiving part, the head can be completely freely pivotable when unlocked, or may still be held by friction so that the shank can be maintained provisionally at a desired angular position. This position can be changed by overcoming the friction force.

Figure 20:
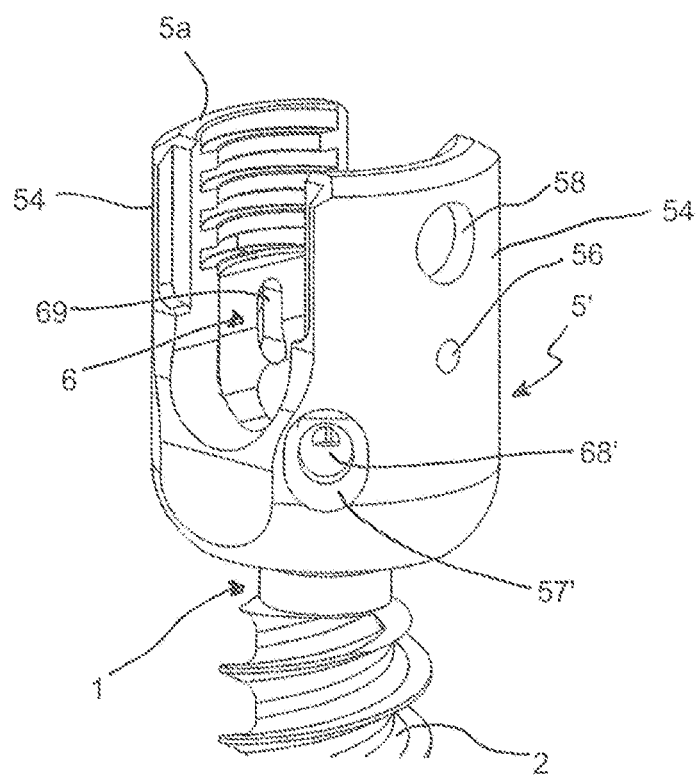
FIG. 20 shows a perspective view of a polyaxial bone anchoring device with a coupling device according to another embodiment.

Another embodiment of the polyaxial bone anchoring device is shown in FIG. 20. The coupling device differs from the coupling device described in the previous embodiment by the design of the receiving part and the pressure member. The receiving part 5' and the pressure member 6' include engagement structures 57' for the receiving part 5' and engagement structures 68' for the pressure member 6' which are offset at an angle different from 90° relative to the longitudinal axis L of the rod receiving recess 53. As shown in FIG. 20, the engagement structures 57', 68' are formed at an angle of 45° or less relative to the rod axis of a rod to be inserted. As in the first embodiment, in each of the receiving part 5' and the pressure member 6', two engagement structures 57', 68' are provided that are offset by 180° in the circumferential direction from one another. Thus, the engagement is effected closer to an inserted rod. Thereby, less space can be used in a direction perpendicular to the rod axis, which may have advantages in certain cases, such as for reducing spreading of a wound or opening during surgery. All other features of the polyaxial bone anchoring device are identical or similar to those of the previous embodiment.

Further modifications of the embodiments described above are also conceivable without departing from the spirit and scope of the invention. For example, the parts are not limited to their detailed shapes as depicted in the embodiments. In particular, the engagement structures at the receiving part and the pressure member may have different shapes, and the shapes of the engagement structure and the instrument may also be different. In some embodiments, one engagement structure on each of the receiving part and the pressure member may be sufficient. An instrument with only one engagement portion can be also sufficient. For the compression of the flexible portion of the pressure member around the head, the narrowing surface may narrow in another shape. For example, a combination of a spherical or bulged shape that abuts against a tapered shape, or a spherical or bulged shape that engages a hollow spherical or hollow bulged shape may also be possible, or even a combination of two cylindrical surfaces.

For the locking member, other known locking members may be used, for example, a two-part locking member that permits locking of the head and the rod separately. The pressure member in this case may have legs that extend above an uppermost surface of the rod. The base forming the rod support surface may also be different, and may for example, be designed to receive only a rod of a single diameter.

The rod used can be any elongate device that is configured to connect two bone anchoring devices. The pressure member and/or the receiving part may also be designed in more than one piece. Also a top loading polyaxial bone anchoring device may be implemented, where the bone anchor can be inserted from the top end of the receiving part. In addition, for the bone anchor, all kinds of bone anchors can be used, such as screws, nails etc.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A system comprising:
 a bone anchor comprising a shank for anchoring in bone and a head;
 a coupling device for coupling a rod to the bone anchor, the coupling device comprising:
  a receiving part having a first end, a second end below the first end, a central axis that extends between the first and second ends, a channel transverse to the central axis at the first end for receiving the rod, a coaxial passage that extends through the receiving part, and an engagement recess extending from outside the receiving part to the passage; and
  a pressure member positionable in the passage to exert pressure on the head, the pressure member having an engagement surface;
  wherein when the head and the pressure member are in the receiving part, the pressure member is movable axially from a first position to a second position to increase the pressure exerted on the head for clamping the head; and
 an instrument comprising an engagement portion configured to engage the engagement recess of the receiving part and to extend through the engagement recess to engage the engagement surface of the pressure member;
 wherein the engagement portion of the instrument is movable transversely towards the central axis of the receiving part to engage and directly exert an axial force directed upwardly towards the first end of the receiving part on the engagement surface of the pressure member to push the pressure member axially upwardly from the second position back towards the first position for decreasing the pressure exerted on the head.

2. The system of claim 1, wherein the instrument further comprises two front portions on which the engagement portion is formed, and wherein the front portions are movable towards one another for engaging the engagement portion with the engagement surface of the pressure member.

3. The system of claim 1, wherein when the pressure member is at the second position, the pressure exerted on the head is configured to lock the head relative to the receiving part.

4. The system of claim 1, wherein the engagement recess of the receiving part includes two holes offset from one another by 180° around the central axis.

5. The system of claim 1, wherein the engagement surface of the pressure member is recessed from a radially outwardly facing surface of the pressure member.

6. The system of claim 1, wherein a surface of the receiving part that defines the engagement recess is inclined relative to the central axis.

7. The system of claim 6, wherein the engagement surface of the pressure member is inclined relative to the central axis.

8. The system of claim 6, wherein at least part of the inclined surface of the receiving part that defines the engagement recess is positioned closer radially to the coaxial passage than to the outside of the receiving part.

9. The system of claim 1, wherein the engagement surface of the pressure member is inclined relative to the central axis.

10. The system of claim 9, wherein the engagement portion of the instrument is configured to engage the inclined portion of the engagement surface of the pressure member to push the pressure member from the second position back towards the first position.

11. The system of claim 1, wherein a surface of the receiving part that defines the engagement recess and the engagement surface of the pressure member each comprises a guiding surface for guiding a portion of the instrument, and wherein the respective guiding surfaces are configured to align with one another when the pressure member is at the first position.

12. The system of claim 1, wherein the engagement recess is at a first side of the channel, and wherein the receiving part further defines another engagement recess at a side of the channel opposite the first side.

13. A system comprising:
 a bone anchor comprising a shank for anchoring in bone and a head;
 a coupling device for coupling a rod to the bone anchor, the coupling device comprising:
  a receiving part having a central axis, an outer surface that extends around the central axis, a channel transverse to the central axis for receiving the rod, a coaxial passage that extends through the receiving part, and an engagement recess that extends laterally from the outer surface to the passage at a first side of the channel, wherein at the first side of the channel, the receiving part further defines a second recess that extends laterally from the outer surface to the passage and a third recess that extends laterally into the outer surface, and wherein the engagement recess, the second recess, and the third recess are shaped differently from and spaced apart from one another; and
  a pressure member positionable in the passage to exert pressure on the head, the pressure member having an engagement surface;
  wherein when the head and the pressure member are in the receiving part, the pressure member is movable axially from a first position to a second position to increase the pressure exerted on the head for clamping the head; and
 an instrument comprising an engagement portion configured to engage the engagement recess of the receiving part and to extend through the engagement recess to engage the engagement surface of the pressure member;
 wherein the engagement portion of the instrument is engageable with the engagement surface of the pressure member to convert transverse movement of the engagement portion towards the central axis of the receiving part into axial movement of at least the engagement surface of the pressure member from the second position back towards the first position for decreasing the pressure exerted on the head.

14. The system of claim 13, wherein the receiving part further defines another engagement recess, another second recess, and another third recess at a side of the channel opposite the first side.

15. The system of claim 13, wherein a wall of the receiving part separates the third recess from the passage.

16. A system comprising:
a bone anchor comprising a shank for anchoring in bone and a head;
a coupling device for coupling a rod to the bone anchor, the coupling device comprising:
a receiving part having a first end, a second end below the first end, a central axis that extends between the first and second ends, an outer surface that extends around the central axis, a channel transverse to the central axis at the first end for receiving the rod, a coaxial passage that extends through the receiving part, and an engagement recess that extends from the outer surface to the passage along a first laterally extending central axis; and
a pressure member positionable in the passage to exert pressure on the head, the pressure member having an engagement surface that defines a second recess that extends along a second laterally extending central axis;
wherein when the head and the pressure member are in the receiving part, the pressure member is movable axially from a first position to a second position to increase the pressure exerted on the head for clamping the head, and wherein when the pressure member is at the second position, the second laterally extending central axis is offset towards the second end relative to the first laterally extending central axis; and
an instrument comprising an engagement portion configured to engage the engagement recess of the receiving part and to extend through the engagement recess to engage the engagement surface of the pressure member;
wherein the engagement portion of the instrument is engageable with the engagement surface of the pressure member to convert transverse movement of the engagement portion towards the central axis of the receiving part into axial movement of at least the engagement surface of the pressure member from the second position back towards the first position for decreasing the pressure exerted on the head.

17. The system of claim 16, wherein when the pressure member is moved from the second position back to the first position, the first and second laterally extending central axes are axially aligned with one another, and wherein a stop is provided for the instrument to adjust the pressure member to the first position.

\* \* \* \* \*

UNITED STATES PATENT AND TRADEMARK OFFICE
CERTIFICATE OF CORRECTION

PATENT NO. : 12,285,193 B2
APPLICATION NO. : 17/569832
DATED : April 29, 2025
INVENTOR(S) : Lutz Biedermann et al.

Page 1 of 1

It is certified that error appears in the above-identified patent and that said Letters Patent is hereby corrected as shown below:

In the Specification

In Column 5, Line 35, delete "Ha" and insert -- $H_a$ --.

In Column 5, Line 36, delete "Ha" and insert -- $H_a$ --.

In Column 7, Line 28, delete "Ha" and insert -- $H_a$ --.

In Column 8, Line 60, delete "Ha" and insert -- $H_a$ --.

Signed and Sealed this
Twenty-second Day of July, 2025

Coke Morgan Stewart
*Acting Director of the United States Patent and Trademark Office*